United States Patent
Do et al.

(10) Patent No.: US 11,373,750 B2
(45) Date of Patent: Jun. 28, 2022

(54) SYSTEMS AND METHODS FOR BRAIN HEMORRHAGE CLASSIFICATION IN MEDICAL IMAGES USING AN ARTIFICIAL INTELLIGENCE NETWORK

(71) Applicant: THE GENERAL HOSPITAL CORPORATION, Boston, MA (US)

(72) Inventors: Synho Do, Lexington, MA (US); Michael Lev, Newton, MA (US); Ramon Gilberto Gonzalez, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/644,779

(22) PCT Filed: Sep. 7, 2018

(86) PCT No.: PCT/US2018/050020
§ 371 (c)(1),
(2) Date: Mar. 5, 2020

(87) PCT Pub. No.: WO2019/051271
PCT Pub. Date: Mar. 14, 2019

(65) Prior Publication Data
US 2021/0082566 A1 Mar. 18, 2021

Related U.S. Application Data
(60) Provisional application No. 62/555,783, filed on Sep. 8, 2017.

(51) Int. Cl.
*G16H 30/40* (2018.01)
*G06T 7/11* (2017.01)
(Continued)

(52) U.S. Cl.
CPC ............. *G16H 30/40* (2018.01); *G06N 3/08* (2013.01); *G06T 5/002* (2013.01); *G06T 7/0012* (2013.01);
(Continued)

(58) Field of Classification Search
CPC ...... G16H 30/40; G16H 50/20; A61B 5/7267; G06T 2207/10024; G06T 2207/30016;
(Continued)

(56) References Cited

U.S. PATENT DOCUMENTS 7,379,572 B2 * 5/2008 Yoshida ................ G06T 7/0012
382/128
2015/0109427 A1 4/2015 Wood et al.
(Continued)

FOREIGN PATENT DOCUMENTS

WO 2017106645 A1 6/2017

OTHER PUBLICATIONS

International Searching Authority, International Search Report and Written Opinion for application PCT/US2018/050020. dated Dec. 7, 2 018.

Primary Examiner — Vu Le
Assistant Examiner — Julius Chai
(74) Attorney, Agent, or Firm — Quarles & Brady LLP

(57) ABSTRACT

Systems and methods for rapid, accurate, fully-automated, brain hemorrhage deep learning (DL) based assessment tools are provided, to assist clinicians in the detection & characterization of hemorrhages or bleeds. Images may be acquired from a subject using an imaging source, and preprocessed to cleanup, reformat, and perform any needed interpolation prior to being analyzed by an artificial intelligence network, such as a convolutional neural network (CNN). The artificial intelligence network identifies and labels regions of interest in the image, such as identifying (Continued)

any hemorrhages or bleeds. An output for a user may also include a confidence value associated with the identification.

18 Claims, 9 Drawing Sheets

(51) Int. Cl.
*G06N 3/08* (2006.01)
*G06T 5/00* (2006.01)
*G06T 7/00* (2017.01)

(52) U.S. Cl.
CPC ...... *G06T 7/11* (2017.01); *G06T 2207/10024* (2013.01); *G06T 2207/30016* (2013.01)

(58) Field of Classification Search
CPC ............. G06T 2207/20081; G06T 7/11; G06T 7/0012; G06T 5/002; G06N 3/08; G06N 20/00; G06N 20/10; G06N 20/20
See application file for complete search history.

(56) References Cited

U.S. PATENT DOCUMENTS

| | | | |
|---|---|---|---|
| 2015/0279034 A1* | 10/2015 | Knapp | G06T 7/0012 382/131 |
| 2016/0350919 A1 | 12/2016 | Steigauf et al. | |
| 2017/0046616 A1* | 2/2017 | Socher | G06N 3/088 |
| 2017/0140236 A1* | 5/2017 | Price | G06K 9/3241 |
| 2018/0315188 A1* | 11/2018 | Tegzes | G06K 9/2054 |
| 2018/0365824 A1* | 12/2018 | Yuh | G06T 7/0012 |

\* cited by examiner

SYSTEMS AND METHODS FOR BRAIN HEMORRHAGE CLASSIFICATION IN MEDICAL IMAGES USING AN ARTIFICIAL INTELLIGENCE NETWORK

CROSS-REFERENCE TO RELATED APPLICATIONS

This application represents the national stage entry of PCT International Application No. PCT/US2018/050020 filed Sep. 7, 2018, which claims the benefit of U.S. Provisional Patent Application Ser. No. 62/555,783, filed on Sep. 8, 2017, and entitled "A METHODOLOGY FOR RAPID, ACCURATE, AND SCRUTINIZABLE BRAIN HEMMORHAGE CLASSIFICATION ARTIFICIAL INTELLIGENCE", incorporated herein by reference in their entirety.

BACKGROUND

Deep learning has demonstrated significant success in improving diagnostic accuracy, speed of image interpretation, and clinical efficiency for a wide range of medical tasks ranging from interstitial pattern detection on chest CT to bone age classification on hand radiographs. Particularly, a data-driven approach with deep neural networks has been actively utilized for several medical image segmentation applications, including segmenting brain tumors on magnetic resonance images, segmenting organs of interest on CT, and segmenting the vascular network of the human eye on fundus photography. These successes are attributed to the capability of deep learning to learn representative and hierarchical image features from data, rather than relying on manually engineered features based on knowledge from domain experts.

However, many deep learning networks are unable to process images at a speed that meets clinical needs and may not be sufficiently accurate to warrant being relied upon in a clinical setting. In still other settings, deep learning routines may not be sensitive enough to distinguish between regions in an image.

SUMMARY OF THE DISCLOSURE

The present disclosure addresses the aforementioned drawbacks by providing a method for identifying a condition in a medical image of a subject. The method includes accessing a medical image of a subject with a computer system. A region-of-interest (ROI) is identified in the medical imaging by processing the medical image with an artificial intelligence (AI) network implemented with a hardware processor and a memory of the computer system. The ROI is labeled with an identification of a first brain hemorrhage condition in the ROI using an output of the AI network. A report is generated for a user identifying the first brain hemorrhage condition and including a confidence value associated with an identification of the first brain hemorrhage condition in the ROI.

It is another aspect of the present disclosure to provide a system for identifying a brain hemorrhage condition in an image of a subject. The system includes at least one hardware processor and a memory. The memory has stored thereon instructions that when executed by the at least one hardware processor cause the at least one hardware processor to perform steps including: (a) accessing a medical image of a subject from the memory; (b) accessing a trained convolutional neural network (CNN) from the memory, the trained CNN having been trained on medical images labeled with one or more different brain hemorrhage conditions; (c) generating a class activation map that indicates at least one brain hemorrhage condition in the medical image by processing the medical image with the AI network; (d) generating a labeled image by labelling regions in the medical image associated with the at least one brain hemorrhage condition using the class activation map; (e) producing at least one confidence value for each labeled region in the labeled image, each confidence value being associated with a confidence of each labeled region representing a corresponding at least one brain hemorrhage condition; and (f) generating a display that depicts the labeled image and the at least one confidence value.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Systems and methods for rapid, accurate, fully-automated brain hemorrhage deep learning (DL) based assessment tools are provided. These systems and methods can be used, as an example, to assist clinicians in the detection and characterization of hemorrhages. Hemorrhages may include intracranial hemorrhage (ICH), subarachnoid hemorrhage (SAH), intra-parenchymal hemorrhage (IPH), epidural/subdural hematoma (SDH), and the like.

Figure 1A:
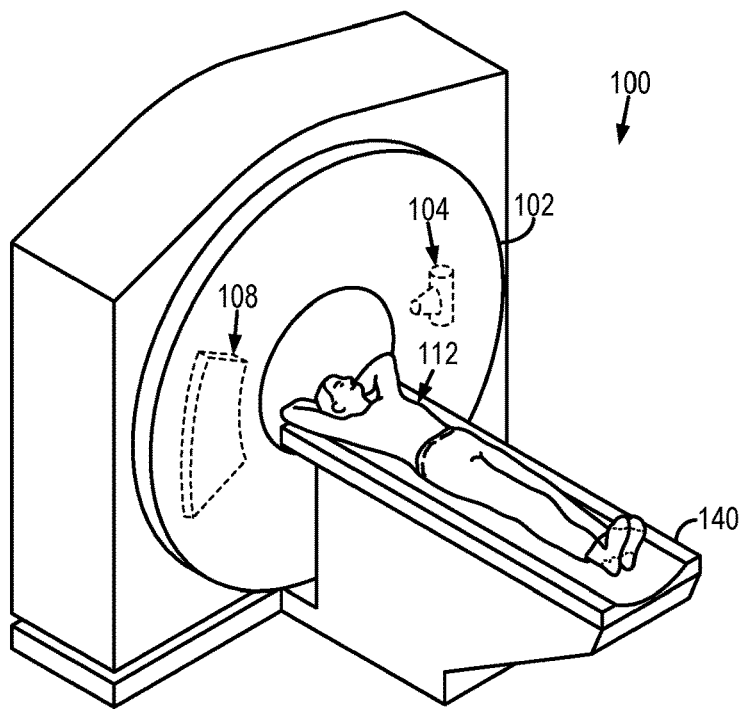
FIGS. 1A and 1B illustrate an example CT system that can be configured to operate some configurations of the present disclosure.
Figure 1B:
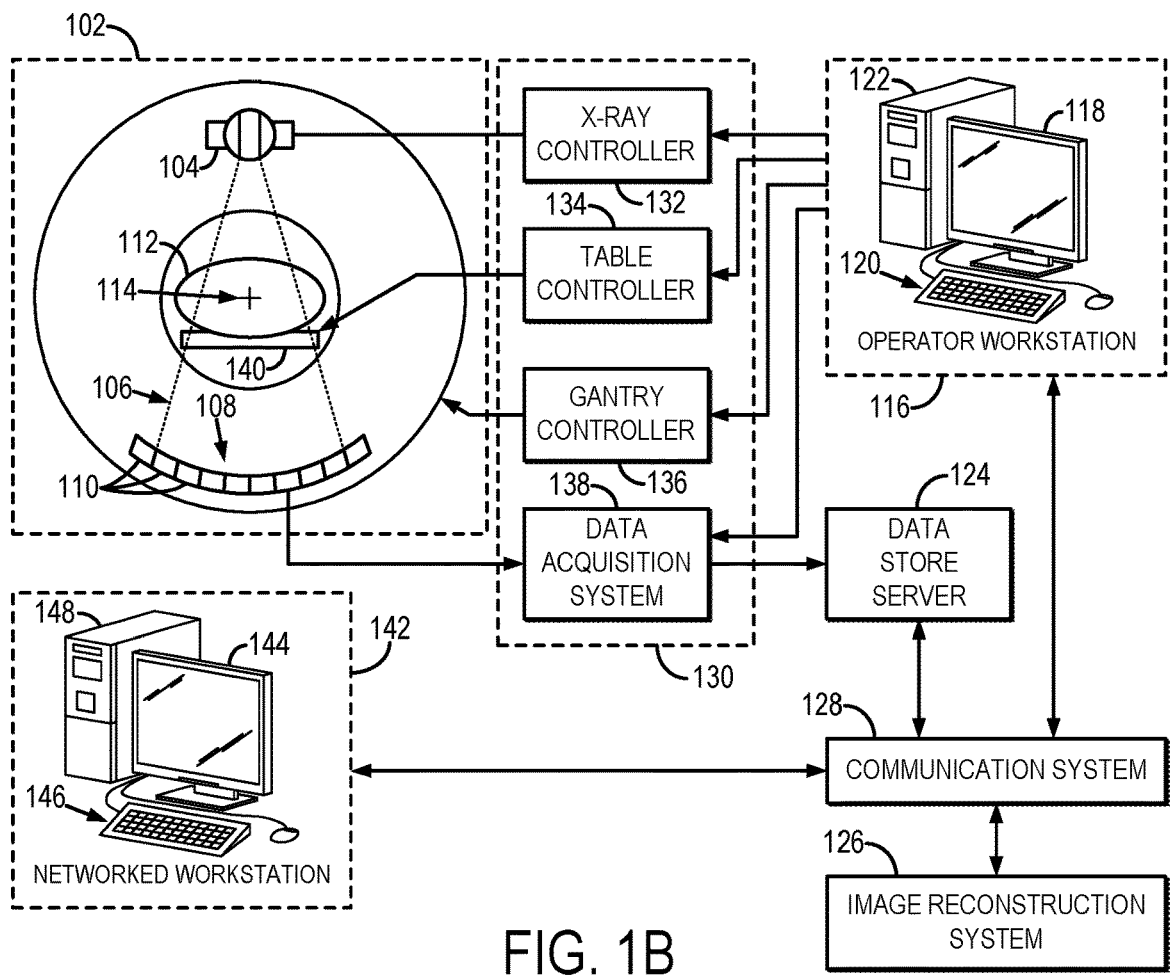

Referring particularly now to FIGS. 1A and 1B, an example of an x-ray computed tomography ("CT") imaging system 100 is illustrated for use with some configurations of the disclosure. The CT system includes a gantry 102, to which at least one x-ray source 104 is coupled. The x-ray source 104 projects an x-ray beam 106, which may be a fan-beam or cone-beam of x-rays, towards a detector array 108 on the opposite side of the gantry 102. The detector array 108 includes a number of x-ray detector elements 110. Together, the x-ray detector elements 110 sense the projected x-rays 106 that pass through a subject 112, such as a medical patient or an object undergoing examination, that is positioned in the CT system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110. In some configurations the system can include a second x-ray source and a second x-ray detector (not shown) operable at a different energy level than x-ray source 104 and detector 110. Any number of x-ray sources and corresponding x-ray detectors operable at different energies may be used, or a single x-ray source 104 may be operable to emit different energies that impinge upon detector 110. During a scan to acquire x-ray projection data, the gantry 102 and the components mounted thereon rotate about a center of rotation 114 located within the CT system 100.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, a gantry controller 136, and a data acquisition system 138. The x-ray controller 132 provides power and timing signals to the x-ray source 104 and the gantry controller 136 controls the rotational speed and position of the gantry 102. The table controller 134 controls a table 140 to position the subject 112 in the gantry 102 of the CT system 100.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
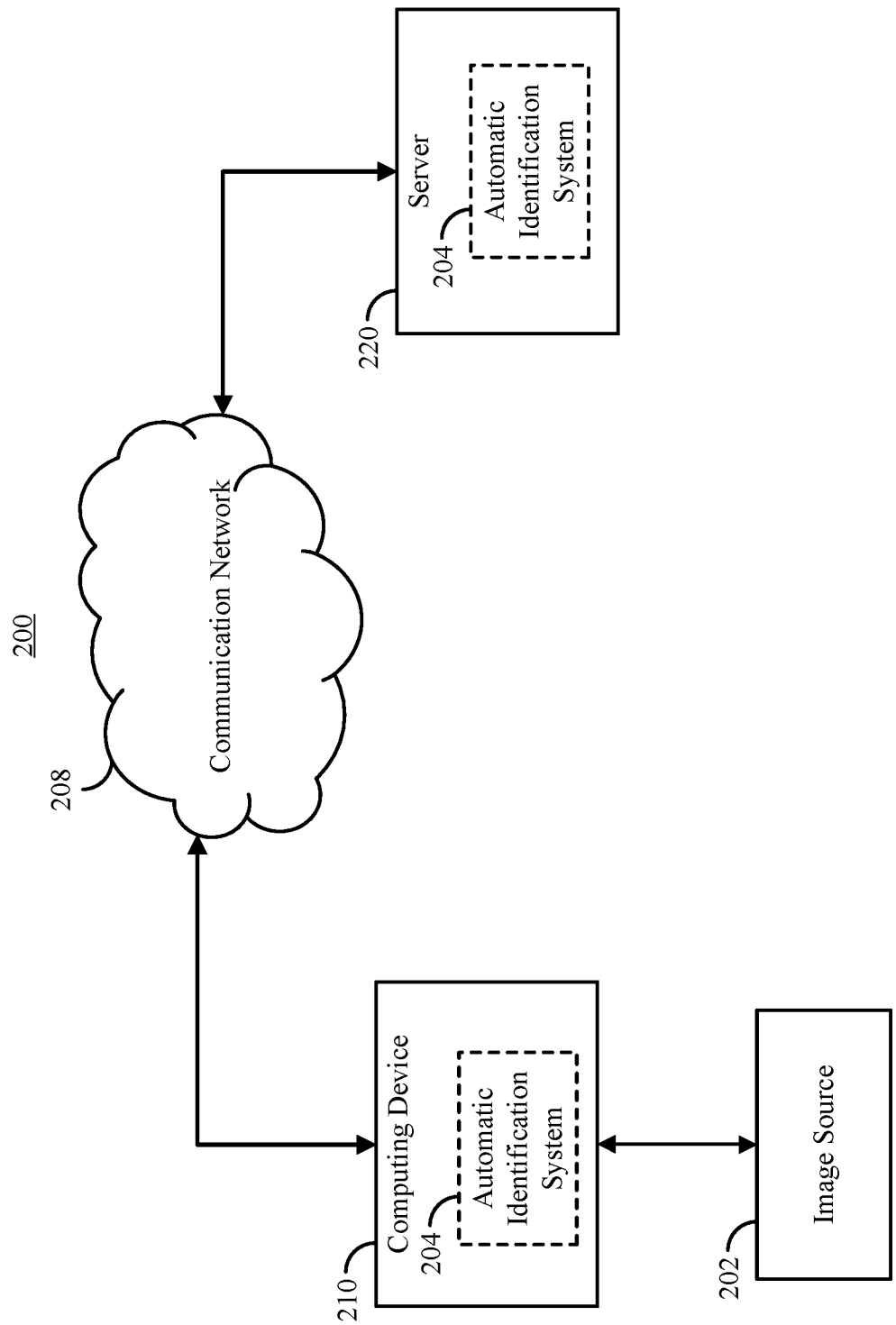
FIG. 2 is a schematic for one configuration of the present disclosure using a computer system.

Referring to FIG. 2, an example 200 of a system for automatically detecting a hemorrhage or a bleed using image data in accordance with some configurations of the disclosed subject matter is shown. A computing device 210 can receive multiple types of image data from image source 202. In some configurations, image source 202 may be a CT system. In some embodiments, computing device 210 can execute at least a portion of an automatic identification system 204 to automatically determine whether a patient condition, such as a hemorrhage, is present in images of a subject.

Additionally or alternatively, in some embodiments, computing device 210 can communicate information about image data received from image source 202 to a server 220 over a communication network 208, which can execute at least a portion of automatic identification system 204. In such embodiments, server 220 can return information to computing device 210 (and/or any other suitable computing device) indicative of an output of automatic identification system 204 to determine whether a clinical condition is present or absent.

In some embodiments, computing device 210 and/or server 220 can be any suitable computing device or combination of devices, such as a desktop computer, a laptop computer, a smartphone, a tablet computer, a wearable computer, a server computer, a virtual machine being executed by a physical computing device, etc. In some embodiments, automatic identification system 204 can extract features from labeled (e.g., labeled as including diseased or normal) image data, such as CT image data, using a convolutional neural network (CNN) trained as a general image classifier.

In some embodiments, image source 202 can be any suitable source of image data, such as a CT machine, another computing device (e.g., a server storing CT image data), etc. In some embodiments, image source 202 can be local to computing device 210. For example, image source 202 can be incorporated with computing device 210 (e.g., computing device 210 can be configured as part of a device for capturing and/or storing images). As another example, image source 202 can be connected to computing device 210 by a cable, a direct wireless link, etc. Additionally or alternatively, in some embodiments, image source 202 can be located locally and/or remotely from computing device 210, and can communicate image data to computing device 210 (and/or server 220) via a communication network (e.g., communication network 208).

In some embodiments, communication network 208 can be any suitable communication network or combination of communication networks. For example, communication network 208 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 208 can be a local area network, a wide area network, a public network (e.g., the Internet), a private or semi-private network (e.g., a corporate or university intranet), any other suitable type of network, or any suitable combination of networks. Communications links shown in FIG. 2 can each be any suitable communications link or combination of communications links, such as wired links, fiber optic links, Wi-Fi links, Bluetooth links, cellular links, etc.

Figure 3:
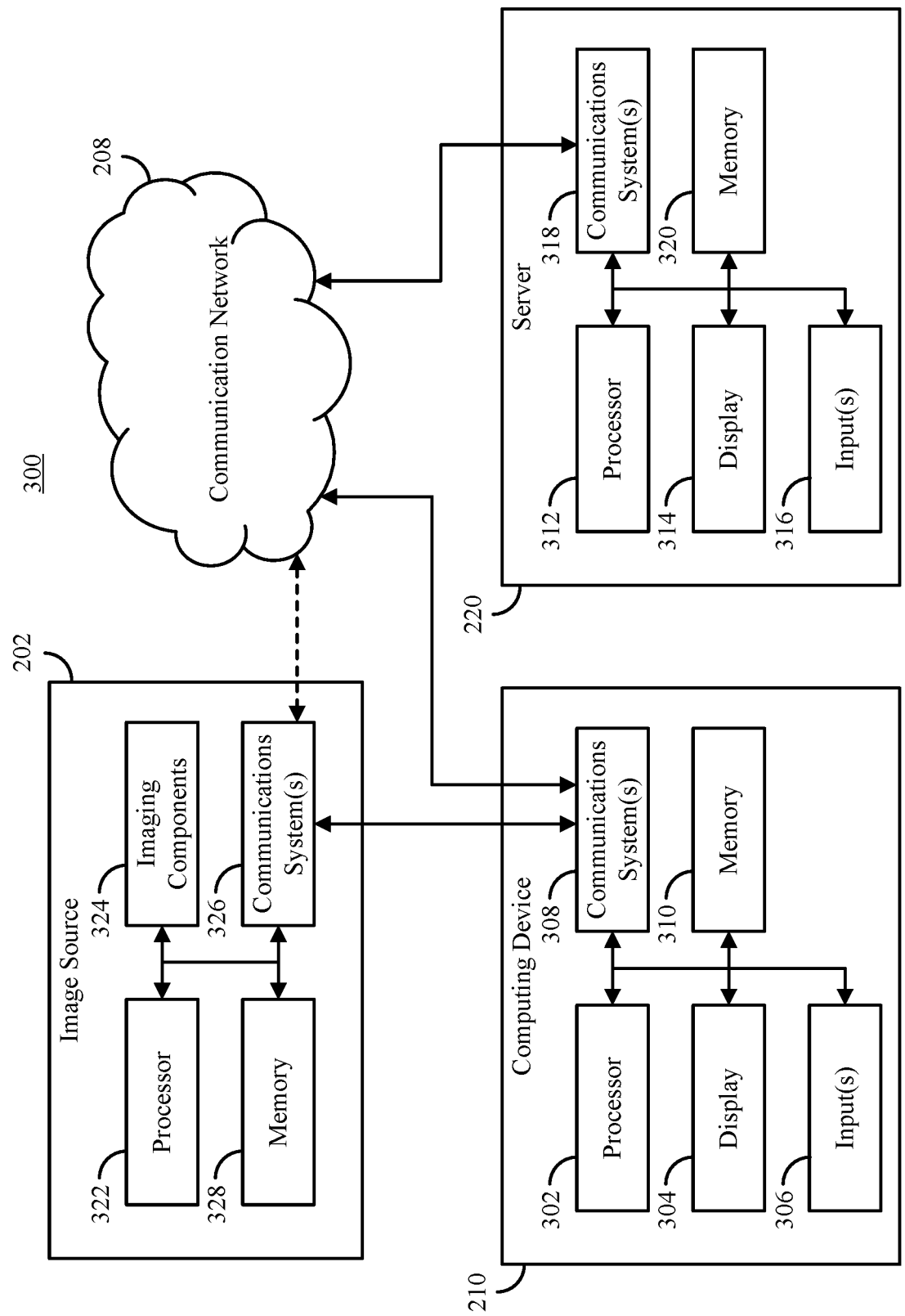
FIG. 3 is another schematic for one configuration of the present disclosure using a computer system.

FIG. 3 shows an example 300 of hardware that can be used to implement image source 202, computing device 210, and/or server 220 in accordance with some embodiments of the disclosed subject matter. As shown in FIG. 3, in some embodiments, computing device 210 can include a processor 302, a display 304, one or more inputs 306, one or more communication systems 308, and/or memory 310. In some embodiments, processor 302 can be any suitable hardware processor or combination of processors, such as a central processing unit (CPU), a graphics processing unit (GPU), etc. In some embodiments, display 304 can include any suitable display devices, such as a computer monitor, a touchscreen, a television, etc. In some embodiments, inputs 306 can include any suitable input devices and/or sensors that can be used to receive user input, such as a keyboard, a mouse, a touchscreen, a microphone, etc.

In some embodiments, communications systems 308 can include any suitable hardware, firmware, and/or software for communicating information over communication network 208 and/or any other suitable communication networks. For example, communications systems 308 can include one or more transceivers, one or more communication chips and/or chip sets, etc. In a more particular example, communications systems 308 can include hardware, firmware and/or software that can be used to establish a Wi-Fi connection, a Bluetooth connection, a cellular connection, an Ethernet connection, etc.

In some embodiments, memory 310 can include any suitable storage device or devices that can be used to store instructions, values, etc., that can be used, for example, by processor 302 to present content using display 304, to communicate with server 220 via communications system(s) 308, etc. Memory 310 can include any suitable volatile memory, non-volatile memory, storage, or any suitable combination thereof. For example, memory 310 can include RAM, ROM, EEPROM, one or more flash drives, one or more hard disks, one or more solid state drives, one or more optical drives, etc. In some embodiments, memory 310 can have encoded thereon a computer program for controlling operation of computing device 210. In such embodiments, processor 302 can execute at least a portion of the computer program to present content (e.g., CT images, user interfaces, graphics, tables, etc.), receive content from server 220, transmit information to server 220, etc.

In some embodiments, server 220 can include a processor 312, a display 314, one or more inputs 316, one or more communications systems 318, and/or memory 320. In some embodiments, processor 312 can be any suitable hardware processor or combination of processors, such as a CPU, a GPU, etc. In some embodiments, display 314 can include any suitable display devices, such as a computer monitor, a touchscreen, a television, etc. In some embodiments, inputs 316 can include any suitable input devices and/or sensors that can be used to receive user input, such as a keyboard, a mouse, a touchscreen, a microphone, etc.

In some embodiments, communications systems 318 can include any suitable hardware, firmware, and/or software for communicating information over communication network 208 and/or any other suitable communication networks. For example, communications systems 318 can include one or more transceivers, one or more communication chips and/or chip sets, etc. In a more particular example, communications systems 318 can include hardware, firmware and/or software that can be used to establish a Wi-Fi connection, a Bluetooth connection, a cellular connection, an Ethernet connection, etc.

In some embodiments, memory 320 can include any suitable storage device or devices that can be used to store instructions, values, etc., that can be used, for example, by processor 312 to present content using display 314, to communicate with one or more computing devices 210, etc. Memory 320 can include any suitable volatile memory, non-volatile memory, storage, or any suitable combination thereof. For example, memory 320 can include RAM, ROM, EEPROM, one or more flash drives, one or more hard disks, one or more solid state drives, one or more optical drives, etc. In some embodiments, memory 320 can have encoded thereon a server program for controlling operation of server 220. In such embodiments, processor 312 can execute at least a portion of the server program to transmit information and/or content (e.g., CT data, results of automatic identification, a user interface, etc.) to one or more computing devices 210, receive information and/or content from one or more computing devices 210, receive instructions from one or more devices (e.g., a personal computer, a laptop computer, a tablet computer, a smartphone, etc.), etc.

In some embodiments, image source 202 can include a processor 322, imaging components 324, one or more communications systems 326, and/or memory 328. In some embodiments, processor 322 can be any suitable hardware processor or combination of processors, such as a CPU, a GPU, etc. In some embodiments, imaging components 324 can be any suitable components to generate image data. An example of an imaging machine that can be used to implement image source 202 can include a conventional CT scanner and the like.

Note that, although not shown, image source 202 can include any suitable inputs and/or outputs. For example, image source 202 can include input devices and/or sensors that can be used to receive user input, such as a keyboard, a mouse, a touchscreen, a microphone, a trackpad, a trackball, hardware buttons, software buttons, etc. As another example, image source 202 can include any suitable display devices, such as a computer monitor, a touchscreen, a television, etc., one or more speakers, etc.

In some embodiments, communications systems 326 can include any suitable hardware, firmware, and/or software for communicating information to computing device 210 (and, in some embodiments, over communication network 208 and/or any other suitable communication networks). For example, communications systems 326 can include one or more transceivers, one or more communication chips and/or chip sets, etc. In a more particular example, communications systems 326 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 328 can include any suitable storage device or devices that can be used to store instructions, values, image data, etc., that can be used, for example, by processor 322 to: control imaging components 324, and/or receive image data from imaging components 324; generate images; present content (e.g., CT images, a user interface, etc.) using a display; communicate with one or more computing devices 610; etc. Memory 328 can include any suitable volatile memory, non-volatile memory, storage, or any suitable combination thereof. For example, memory 328 can include RAM, ROM, EEPROM, one or more flash drives, one or more hard disks, one or more solid state drives, one or more optical drives, etc. In some embodiments, memory 328 can have encoded thereon a program for controlling operation of image source 202. In such embodiments, processor 322 can execute at least a portion of the program to generate images, transmit information and/or content (e.g., CT image data) to one or more computing devices 210, receive information and/or content from one or more computing devices 210, receive instructions from one or more devices (e.g., a personal computer, a laptop computer, a tablet computer, a smartphone, etc.), etc.

Figure 4:
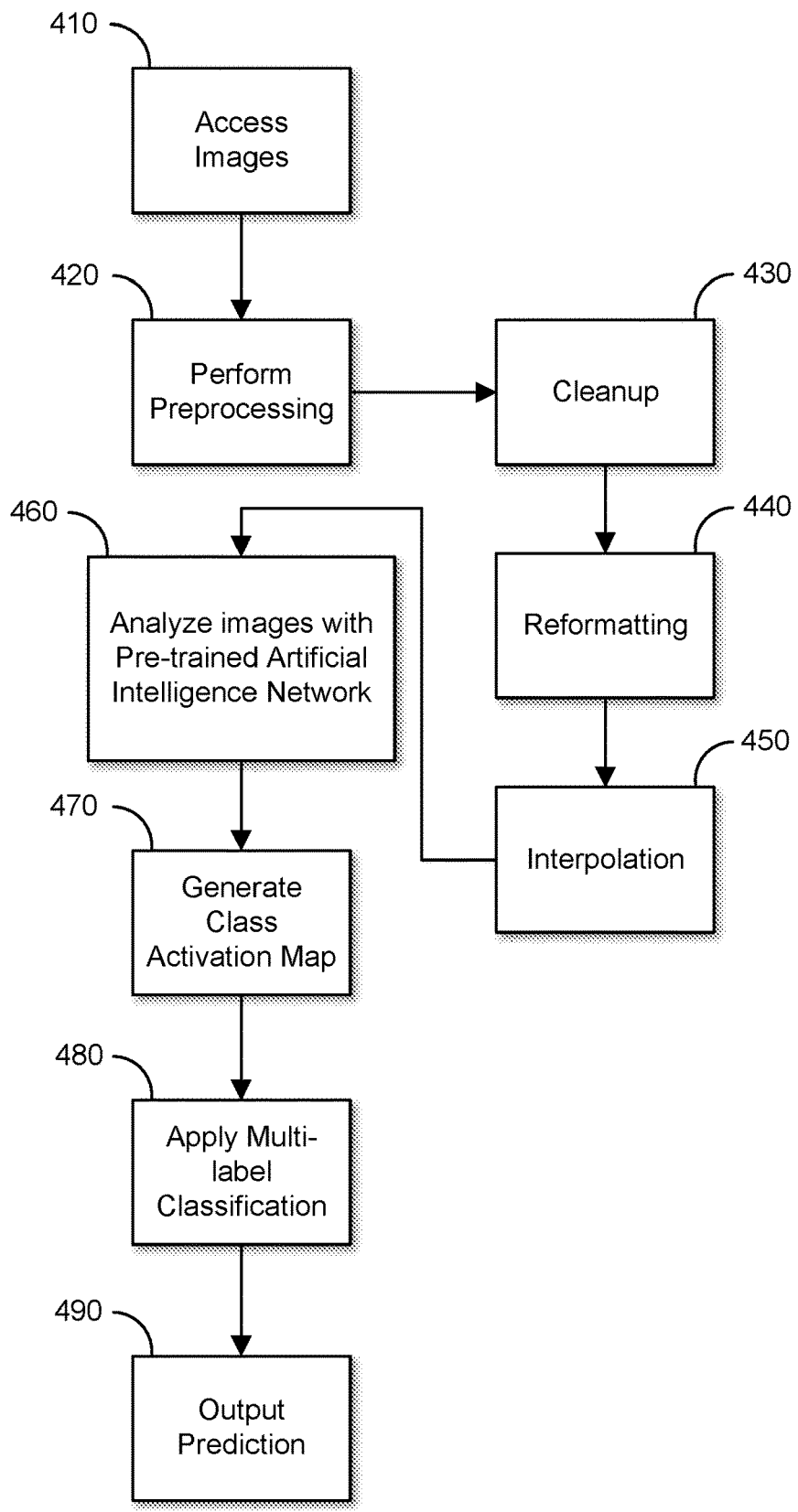
FIG. 4 is a flowchart depicting one configuration of the disclosure for identifying hemorrhages or bleeds using a convolutional neural network (CNN).

Referring to FIG. 4, a flowchart is shown for one configuration of the disclosure. At step 410, images acquired from a subject using an imaging source, such as a CT system, are accessed. Accessing the images can include acquiring the images with the imaging source, or can include accessing or otherwise retrieving previously acquired images that are stored in a PACS, a memory, or another suitable data storage. The accessed image can include an image volume. The image volume may include a three-dimensional image volume containing a plurality of spatially adjacent image slices. The image volume may also include a series of temporally adjacent images, such as those acquired as a time series of images from one or more image slice locations. The images may be images acquired with a CT system, an MRI system, or any other suitable medical imaging system.

The images may be preprocessed, as indicated at process block 420. Preprocessing of the acquired images may include cleanup of the images at step 430, reformatting of the images at step 440, and interpolation at step 450. Image cleanup at step 430 may include applying masks to the image to localize specific regions of interest for the CNN to process, and may include removing background signal from the images.

Figure 5:
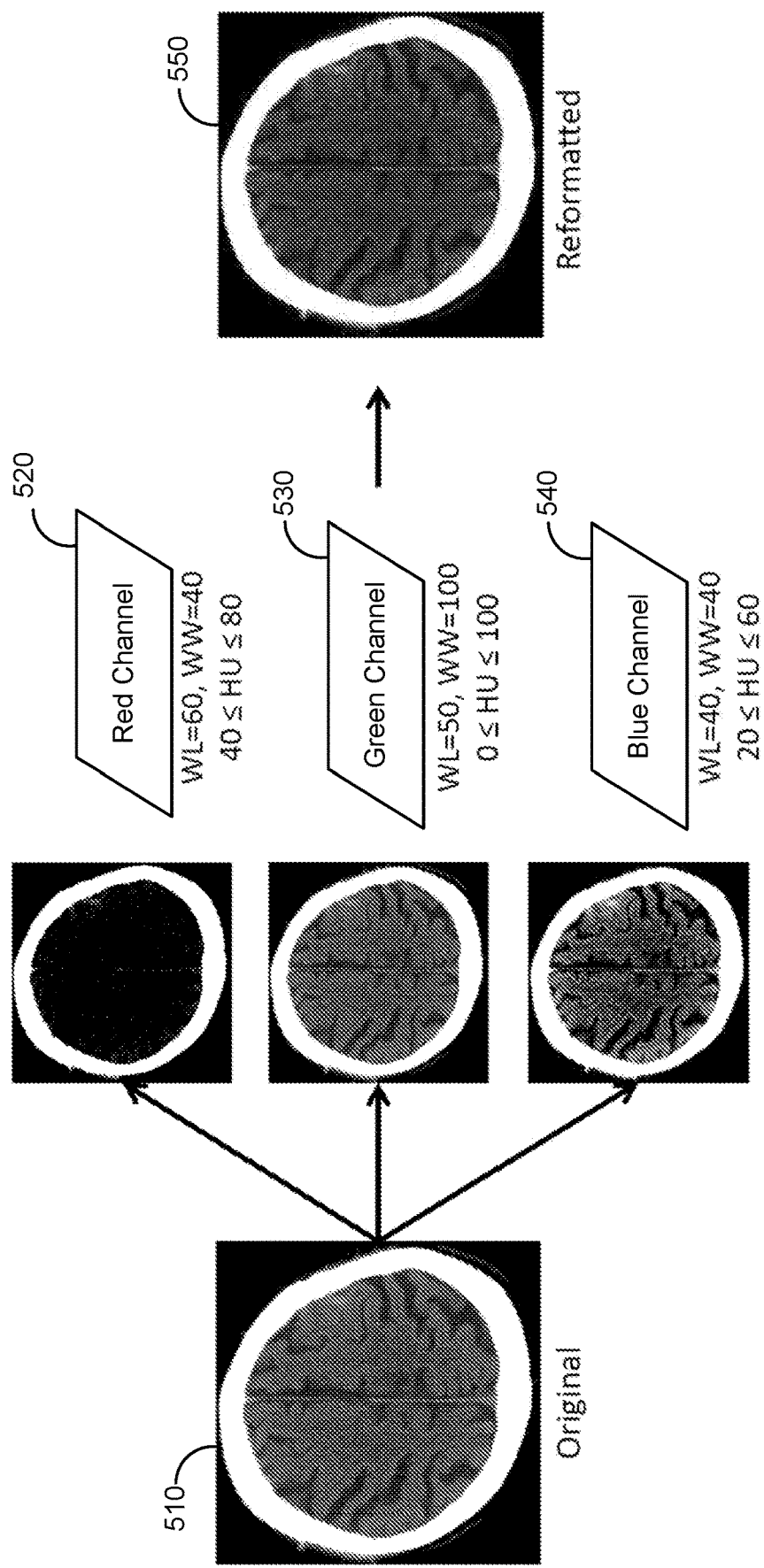
FIG. 5 is a schematic for one configuration of window leveling an original image into multiple color channels that are then combined for creating a reformatted image.

Referring to FIG. 5, the image reformatting performed at step 440 in FIG. 4 may include applying different window/level settings to the input image 510 in order to generate multiple different channel images 512. Each channel image can be generated by applying a specified window/level setting to pixels in the input image 510. For instance, a specified window/level setting can be applied to pixels having intensity values in a specified range associated with the specified window. As another example, a specified window/level setting can be applied to pixels having quantitative values, such as Hounsfield Units (HU), within a specified range associated with the specified window. Any number of channel images may be generated, and a reformatted image 550 can be created by combining the channel images.

In some implementations, the different channel images may be colorized, such as mapping pixel intensity values in the channel images to one or more different color scales, or by otherwise assigning a specific color to each different channel image. For example, a red channel image 520 may be generated using a window/level setting with a level WL=60 and window WW=40 for pixels in the input image 510 corresponding to HU values in the range of 40-80. The pixel values in the red channel image 520 are then assigned a suitable RGB value, such as by mapping the pixel values to an RGB color scale. A green channel image 530 may be generated using a window/level setting with a level WL=50 and a window WW=100 for pixels in the input image 510 corresponding to HU values in the range of 0-100. The pixel values in the green channel image 530 are then assigned a suitable RGB value, such as by mapping the pixel values to an RGB color scale. A blue channel image 540 may be generated using a window/level setting with a level WL=40 and a window WW=40 for pixels in the input image 510 corresponding to HU values in the range of 20-60. The pixel values in the blue channel image 540 are then assigned a suitable RGB value, such as by mapping the pixel values to an RGB color scale. When the different channel images are assigned different colors (e.g., by converting grayscale values to RGB values, or values from a different colormap or color scale), the reformatted image 550 may be stored or presented to a user as a multi-color image. In some instances, the channel images can be combined to form a combined image (e.g., an RGB image when combining red, green, and blue channel images).

Figure 6:
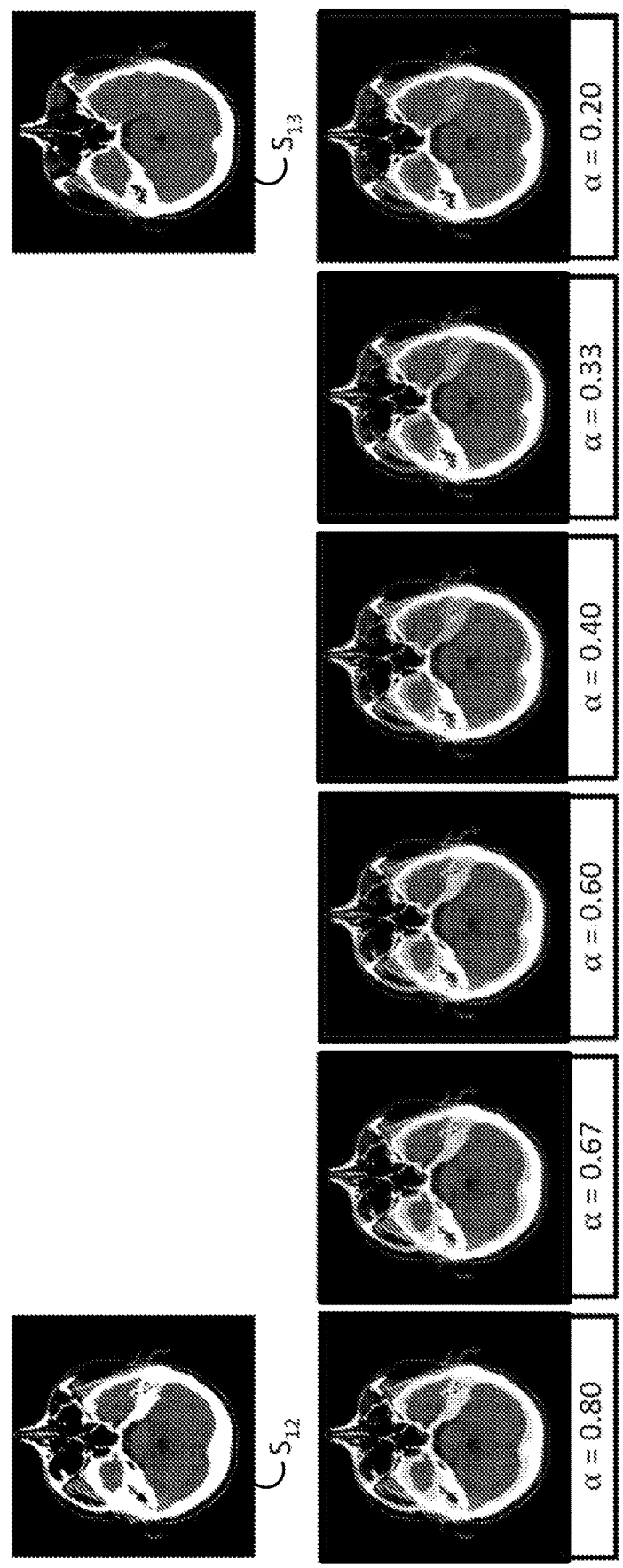
FIG. 6 is a depiction of image slice interpolation that may be used in one configuration of the present disclosure.

Image interpolation performed at step 450 of FIG. 4 may be performed to model data between slices. This form of interpolation may also be used when creating 3D models from a series of 2D images where there is a desire to increase the resolution of the series of 2D images by reducing the space between slices. A new interpolated slice may be created as follows:

$$S_{interpolation} = \alpha S_1 + (1-\alpha) S_2 \qquad (1);$$

where $(0 \leq \alpha \leq 1)$, $\alpha$ is a mixing weight that may be based on the number of desired interpolated slices and the proximity of the created slice in the stack to either $S_1$ or $S_2$; $S_1$ is a first original slice, $S_2$ is a second original slice, and $S_{interpolation}$ is the interpolated slice situated between $S_1$ and $S_2$. Referring to FIG. 6, an example is shown where six slices are desired between a first original slice $S_{12}$ and a second original slice $S_{13}$ where $\alpha$ may be 0.80, 0.67, 0.60, 0.40, 0.33, and 0.20 for each of the six slices shown between $S_{12}$ and $S_{13}$. In some implementations, the same mixing weight can be used for each interpolation; however, in some other implementations one or more different mixing weights can be used for different interpolation steps. For instance, a first mixing weight may be used when interpolating between a first and second slice, but a second mixing weight that is different from the first may be used when interpolating between the second slice and a third slice.

Referring again to FIG. 4, the processed images are then input to and analyzed by the artificial intelligence (AI) network, which may be a convolutional neural network (CNN), at step 460. The AI network is generally implemented with one or more hardware processors and one or more memories. In some implementations, real-time data augmentation may be performed on the processed images before they are input into the AI network. Real-time augmentation may include horizontal flipping, rescaling, rotation, denoising, and the like. The AI network may be previously trained using labelled or annotated images prior to analyzing images acquired from the subject. Labelled or annotated images may include, for instance, images in which regions-of-interest have been identified and to which a label or annotation has been assigned. In some instances, a labelled or annotated image can include an image that has been suitably modified to include such labels or annotations. As one example, the labelled or annotated regions could be color coded. In some other instances, the labelled or annotated images could include a separate image or map that depicts the corresponding locations of the labelled or annotated regions. As one example, the separate image or map could be a class activation map, such as those generated when implementing the systems and methods described in the present disclosure. As noted, in some embodiments, the AI network can be a CNN. The CNN could be implemented using an ImageNet CNN, a GoogleNet CNN, a VGG16 CNN, and so on.

Class activation maps are generated at step 470 as an output from the AI network and are used to identify and label different regions or objects of interest in the images at step 480. The identifying and labeling process may include labeling hemorrhages, such as IPH, ICH, IVH, SDH, and SAH. A bleed may also be identified and labeled. Using a "bleed" label and in some instances improve the sensitivity of the analysis. The different labels can be generated using different loss penalties to overcome class imbalance.

At step 490, a prediction is output for a user indicating the results of the identification and labeling processes and may include a confidence value associated with the identification. Confidence values may be reported between 0-100 in percent, or may be reported between 0-1, or in another form. For example, the output may indicate the presence of a SAH in a particular region of the image with a 99% confidence value. Alternatively, the output may indicate the results and associated confidence values for all of the potential hemorrhages or bleeds. For example, the output could include IPH=1%, IVH=1%, SDH=3%, SAH=95%, bleed=0%, along with a corresponding image highlighting the one or more regions that were identified as being of interest. A particular subject may suffer from multiple hemorrhages of bleeds, which may each fall into different classifications.

Figure 7A:
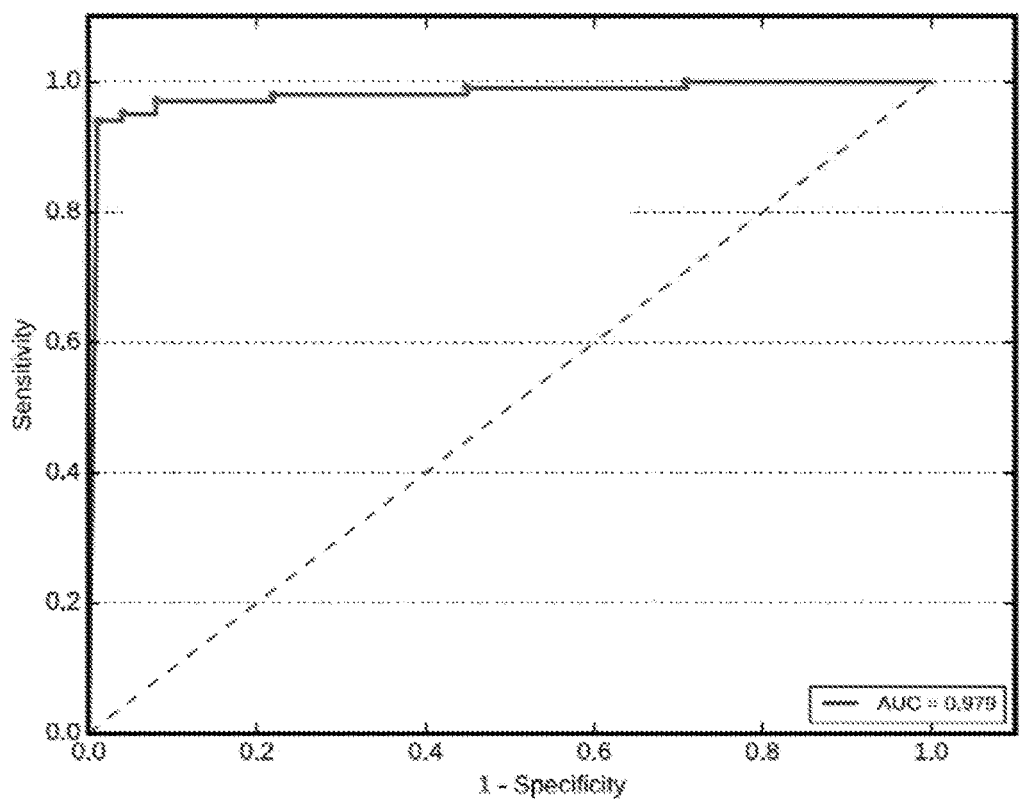
FIG. 7A is a graph representation of the results of an example binary classification scheme using a receiver operating characteristics (ROC) curve analysis.
Figure 7B:
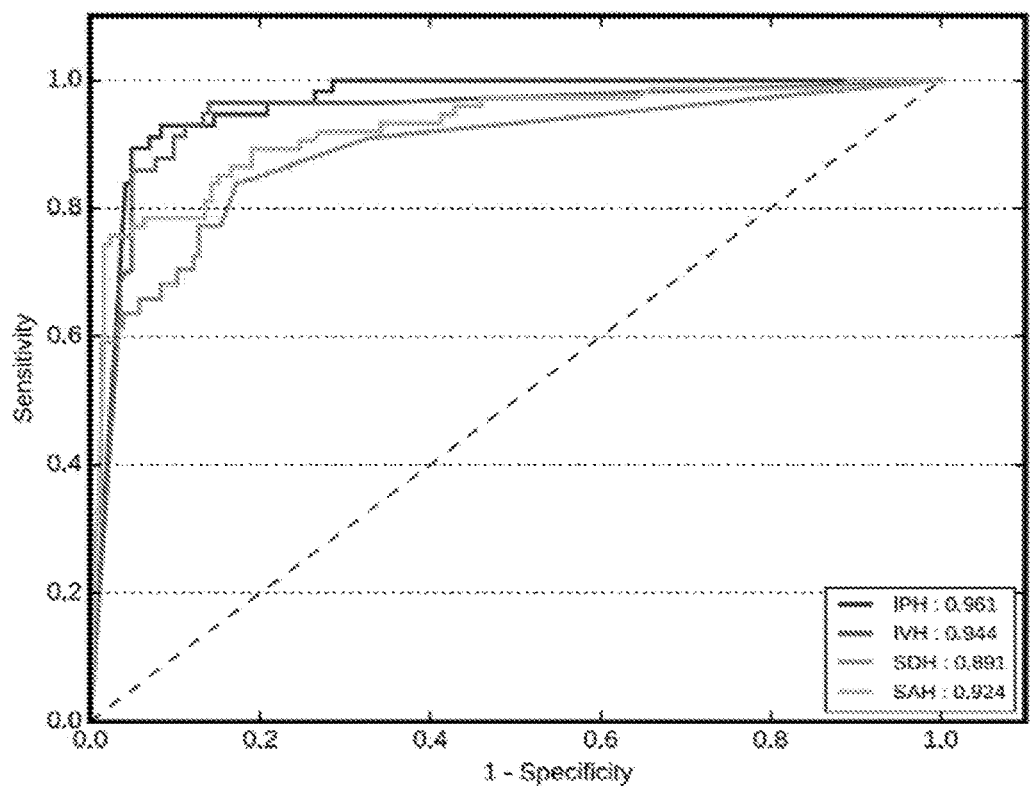
FIG. 7B is a graph representation of the results of an example multi-label classification approach according to one configuration of the disclosure using a receiver operating characteristics (ROC) curve analysis.

Referring to FIGS. 7A and 7B, an example receiver operating characteristics (ROC) curve is shown in FIG. 7A where true-positive rate (sensitivity) is plotted against 1-specificity for a binary classification method. An area under the curve (AUC) of the ROC helps define the diagnostic capabilities of a method. FIG. 7B displays example results of a multi-label classification as discussed in FIG. 4 with a similar ROC curve analysis. AUC values are comparable for different hemorrhage identifications. A similar AUC analysis of an ROC curve may be used as an output to a user at step 490 in FIG. 4 in addition to or in place of the confident values.

In one example of the present disclosure, a retrospective study was conducted. A PACS system was searched for unenhanced head CTs of IPH, SAH, and SDH/EDH. Two radiologists reviewed the scans and selected slices with hemorrhage for training. The training set was enriched with cases that had subtle or small volume bleeds. 100 slices were randomly selected from each class for validation, independent of the training set. Full resolution 512×512 pixel CT images were converted into gray levels by applying a brain CT window setting (window-level=50 HU, window-width=100 HU). A Transfer learning methodology was applied using a customized (weight initialized) ImageNet pre-trained Convolutional Neural Network (CNN), fine-tuned on the training dataset.

A total of 1058 normal, 412 SAH, 287 IPH, 414 SDH, and 233 EDH head CT slices were collected from 36 normal, 46 SAH, 50 IPH, 25 SDH, and 25 EDH patients. AUC for detection of hemorrhage was 0.96 for normal patients, 0.90 for SAH, 0.95 for IPH, 0.89 for SDH, and 0.98 for EDH. The deployment time for full head CT 3D-volume assessment was taken less than 2-sec (mean) for all slices. These results reflect a high accuracy for the detection and characterization of intracranial hemorrhage. Results for the example study are shown in Table 1.

TABLE 1

| Label | Accession Numbers | | Patients | | Axial Slices | |
| --- | --- | --- | --- | --- | --- | --- |
| | Count | Proportion (%) | Count | Proportion (%) | Count | Proportion (%) |
| IPH | 401 | 47 | 280 | 38 | 2750 | 23 |
| IVH | 184 | 22 | 140 | 19 | 1571 | 13 |
| SDH | 47 | 6 | 43 | 6 | 401 | 3 |
| EDH | 1 | 0 | 1 | 0 | 4 | 0 |
| SAH | 269 | 32 | 248 | 34 | 1350 | 11 |
| BGC | 91 | 11 | 88 | 12 | 218 | 2 |
| No Bleed | 206 | 24 | 206 | 28 | 7044 | 60 |
| Bleed | 578 | 68 | 455 | 62 | 4606 | 39 |
| NoBleed | 275 | 32 | 275 | 38 | 7212 | 61 |
| Total | 853 | 100 | 730 | 100 | 11818 | 100 |

Data was split in the example study among a training set, a validation set, and a test set. The data split for the training set is reflected in Table 2. The data split for the validation set is reflected in Table 3. The data set for the test set is reflected in Table 4.

TABLE 2

| Type | | #PID | #ACC | # Slices |
| --- | --- | --- | --- | --- |
| Bleed | IPH | 218 | 339 | 2251 |
| | IVH | 85 | 116 | 1250 |
| | SDH | 12 | 16 | 225 |
| | SAH | 164 | 176 | 1021 |
| | Total | 354 | 477 | 3682 |
| No Bleed | BGC | 48 | 48 | 104 |
| | None | 122 | 122 | 4176 |
| | Total | 170 | 170 | 4280 |
| Total | | 524 | 647 | 7962 |

TABLE 3

| Type | | #ACC (#PID) | # Slices |
| --- | --- | --- | --- |
| Bleed | IPH | 62 | 499 |
| | IVH | 35 | 321 |
| | SDH | 24 | 171 |
| | SAH | 63 | 329 |
| | Total | 100 | 919 |
| No Bleed | BGC | 21 | 64 |
| | None | 79 | 2688 |
| | Total | 100 | 2752 |
| Total | | 200 | 3667 |

TABLE 4

| Type | | #ACC (#PID) |
|---|---|---|
| Bleed | IPH | 57 |
| | IVH | 59 |
| | SDH | 44 |
| | SAH | 74 |
| | EDH | 19 |
| | Total | 100 |
| No Bleed | Total | 100 |
| Total | | 200 |

Figure 8:
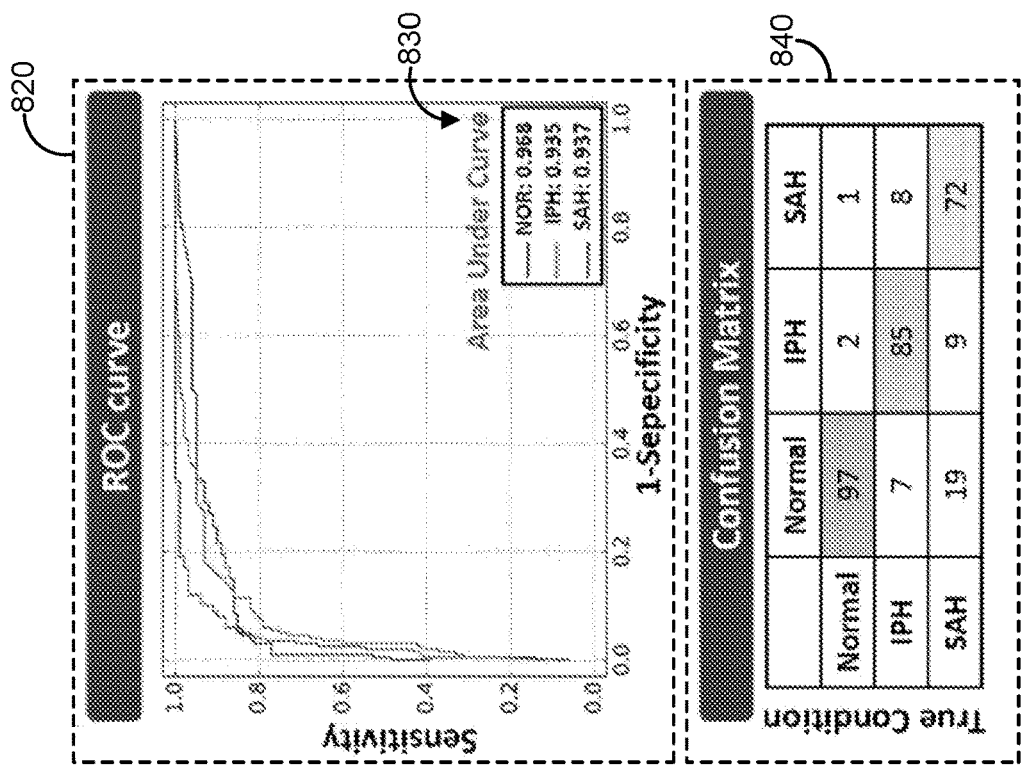
FIG. 8 is a depiction of an example output report for one configuration showing the results of a confidence analysis.
Figure 8:
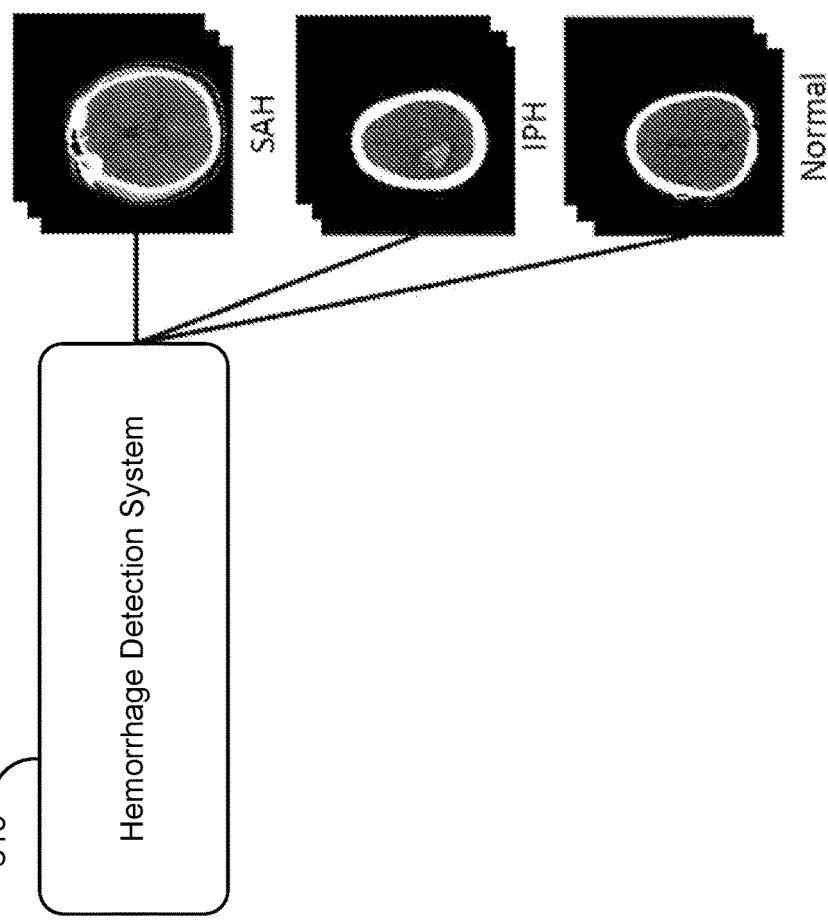

Referring to FIG. 8, one configuration for displaying results of a hemorrhage detection system 810 for a user is shown. Example ROC curve analysis 820 displays the results of the above study, but is presented here as an example of how an ROC graph may be displayed for a user with AUC analysis report 830. The results of the study above are also reflected in the confusion matrix report 840. This confusion matrix represents the likelihood for a particular hemorrhage or condition to be reported accurately and not to be confused with a different hemorrhage or condition.

Figure 9:
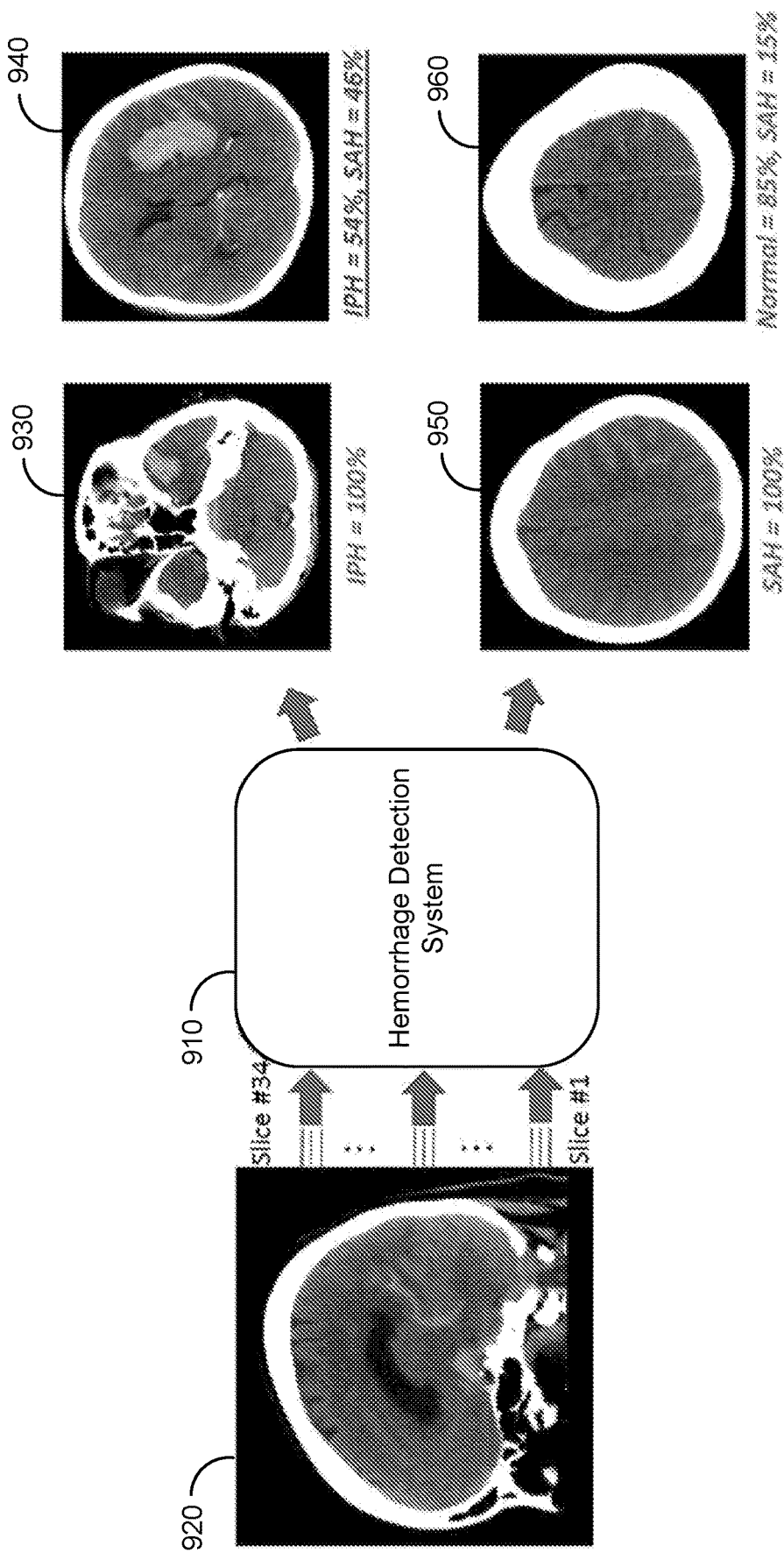
FIG. 9 is a depiction of an example output report for one configuration involving multiple hemorrhages identified by slice location.

Referring to FIG. 9, one configuration for reporting the results for a patient that presents with multiple hemorrhages or conditions is shown. Original image 920 shows a patient presenting with both SAH and IPH. This image is input to the hemorrhage detection system 910 which follows the analysis of FIG. 4. The multiple hemorrhages are identified by slice and reported with a corresponding confidence value. For example, with the patient with original image 920 depicted, slice 930 reports an IPH with 100% confidence. Slice 940 reflects a mix of IPH at 54% confidence and SAH with 46% confidence. Slice 950 reflects SAH with 100% confidence, and slice 960 reflects normal with 85% confidence and SAH with 15% confidence. These are examples, and one skilled in the art will appreciate that different original images from different patients will present with different results, include a report of any of the hemorrhages or conditions as described previously.

The present disclosure has described one or more preferred embodiments, and it should be appreciated that many equivalents, alternatives, variations, and modifications, aside from those expressly stated, are possible and within the scope of the invention.

The invention claimed is:

1. A method for identifying a condition in a medical image of a subject comprising:
 a) accessing a medical image of a subject with a computer system;
 b) generating a plurality of channel images from the medical image, each channel image being generated by applying at least one of a window setting and a level setting to the medical image based on a color, or color intensity;
 c) identifying a region-of-interest (ROI) in the medical image by processing the plurality of channel images with an artificial intelligence (AI) network implemented with a hardware processor and a memory of the computer system;
 d) labelling the ROI with an identification of a first brain hemorrhage condition in the ROI using an output of the AI network; and
 e) generating a report for a user identifying the first brain hemorrhage condition and including a confidence value associated with an identification of the first brain hemorrhage condition in the ROI.

2. The method of claim 1 wherein the first brain hemorrhage condition includes at least one of an intracranial hemorrhage (ICH), an intraventricular hemorrhage (IVH), a subarachnoid hemorrhage (SAH), an intra-parenchymal hemorrhage (IPH), an epidural hematoma (EDH), a subdural hematoma (SDH), or a bleed.

3. The method of claim 1 further comprising identifying a second ROI in the medical imaging by processing the medical image with the AI network, and labelling the second ROI with an identification of a second brain hemorrhage condition using an output of the AI network.

4. The method of claim 3 wherein generating the report includes displaying a first image slice in which the first brain hemorrhage condition is identified and displaying a second image slice in which the second brain hemorrhage condition is identified.

5. The method of claim 3 wherein generating the report includes displaying an image slice in which both the first brain hemorrhage condition and the second brain hemorrhage condition are identified, and wherein identifying the second condition includes a second confidence value associated with an identification of the second brain hemorrhage condition in the second ROI.

6. The method of claim 1 wherein the plurality of channel images are combined to form a combined image and inputting the plurality of channel images to the AI network comprises inputting the combined image to the AI network.

7. The method of claim 1 wherein each of the plurality of channel images is assigned a different color.

8. The method of claim 7 wherein each of the plurality of channel images is assigned the different color by mapping pixel intensities in each channel image to a different color scale.

9. The method of claim 8 wherein the plurality of channel images comprises a first channel image, a second channel image, and a third channel image, and wherein pixel intensities in the first channel image are mapped to a red color scale, pixel intensities in the second channel image are mapped to a green color scale, and pixel intensities in the third channel image are mapped to a blue color scale.

10. The method of claim 1 further comprising preprocessing the medical image prior to inputting the medical image to the AI network, wherein preprocessing the medical image includes reducing noise in the medical image.

11. The method of claim 1 wherein the medical image is an image volume comprising a plurality of image slices, and wherein the plurality of image slices are interpolated before inputting the medical image to the AI network.

12. The method of claim 11 wherein the plurality of image slices are interpolated to generate at least one new image slice between two of the plurality of image slices.

13. The method of claim 11 wherein the image volume is a three-dimensional image volume comprising a stack of spatially adjacent image slices.

14. The method of claim 11 wherein the image volume comprises a series of temporally adjacent image slices.

15. The method of claim 1 wherein the AI network is a convolutional neural network.

16. The method of claim 1 wherein the output of the AI network comprises a class activation map.

17. A system for identifying a brain hemorrhage condition in an image of a subject comprising:
 at least one hardware processor;

a memory having stored thereon instructions that when executed by the at least one hardware processor cause the at least one hardware processor to perform steps comprising:
  a) accessing a medical image of a subject from the memory;
  b) generating a plurality of channel images from the medical image, each channel image being generated by applying at least one of a window setting and a level setting to the medical image based on a color, or color intensity;
  c) accessing a trained convolutional neural network (CNN) from the memory, the trained CNN having been trained on medical images labeled with one or more different brain hemorrhage conditions;
  d) generating a class activation map that indicates at least one brain hemorrhage condition in the medical image by processing the plurality of channel images with the AI network;
  e) generating a labeled image by labelling regions in the medical image associated with the at least one brain hemorrhage condition using the class activation map;
  f) producing at least one confidence value for each labeled region in the labeled image, each confidence value being associated with a confidence of each labeled region representing a corresponding at least one brain hemorrhage condition; and
  g) generating a display that depicts the labeled image and the at least one confidence value.

18. The system of claim 17 wherein the at least one brain hemorrhage condition includes at least one of an intracranial hemorrhage (ICH), an intraventricular hemorrhage (IVH), a subarachnoid hemorrhage (SAH), an intra-parenchymal hemorrhage (IPH), an epidural hematoma (EDH), a subdural hematoma (SDH), or a bleed.

* * * * *